(12) United States Patent
Donnelly et al.

(10) Patent No.: US 8,449,584 B2
(45) Date of Patent: May 28, 2013

(54) ABSORBABLE BONE ANCHOR

(75) Inventors: Lisa M. Donnelly, Wayland, MA (US);
 Edwin C. Bartlett, Mansfield, MA (US);
 Karl S. Reese, West Roxbury, MA (US);
 Steven D. Muller, Mansfield, MA (US);
 Paul J. Ares, Norton, MA (US)

(73) Assignee: DePuy Mitek, LLC, Raynham, MA (US)

( * ) Notice: Subject to any disclaimer, the term of this patent is extended or adjusted under 35 U.S.C. 154(b) by 114 days.

(21) Appl. No.: 12/968,939

(22) Filed: Dec. 15, 2010

(65) Prior Publication Data
US 2011/0087283 A1    Apr. 14, 2011

Related U.S. Application Data

(63) Continuation of application No. 10/888,179, filed on Jul. 9, 2004, now Pat. No. 7,875,064, which is a continuation of application No. 09/967,473, filed on Sep. 28, 2001, now Pat. No. 6,773,436.

(51) Int. Cl.
 *A61B 17/84* (2006.01)

(52) U.S. Cl.
 USPC .............................. 606/300; 606/77

(58) Field of Classification Search
 USPC .................................. 606/77, 300
 See application file for complete search history.

(56) References Cited

U.S. PATENT DOCUMENTS

| | | | |
|---|---|---|---|
| 4,045,418 A | 8/1977 | Sinclair | |
| 4,057,537 A | 11/1977 | Sinclair | |
| 4,105,034 A | 8/1978 | Shalaby et al. | |
| 4,130,639 A | 12/1978 | Shalaby et al. | |
| 4,140,678 A | 2/1979 | Shalaby et al. | |
| 4,141,087 A | 2/1979 | Shalaby et al. | |
| 4,205,399 A | 6/1980 | Shalaby et al. | |
| 4,208,511 A | 6/1980 | Shalaby et al. | |
| 4,590,928 A | 5/1986 | Hunt et al. | |
| 4,851,005 A | 7/1989 | Hunt et al. | |
| 4,898,156 A | 2/1990 | Gatturna et al. | |
| 5,259,846 A | 11/1993 | Granger et al. | |
| 5,312,438 A | 5/1994 | Johnson | |
| 5,417,712 A | 5/1995 | Whittaker et al. | |
| 5,464,929 A | 11/1995 | Bezwada et al. | |
| 5,468,253 A | 11/1995 | Bezwada et al. | |
| 5,470,334 A | 11/1995 | Ross et al. | |
| 5,522,845 A | 6/1996 | Wenstrom, Jr. | |
| 5,595,751 A | 1/1997 | Bezwada et al. | |

(Continued)

FOREIGN PATENT DOCUMENTS

WO         0051497 A1     9/2000

OTHER PUBLICATIONS

Aycock, The Encyclopedia of Polymer Science, vol. 13, pp. 31-41, Wiley Intersciences, John Wiley & Sons, 1988.

(Continued)

*Primary Examiner* — Nicholas Woodall (57) ABSTRACT

A bone anchor is provided that can toggle in two planes for secure anchorage within a bone cavity. The bone anchor includes an oblique suture channel configured such that a suture strand extending through the bone anchor can be tensioned to toggle the bone anchor inside the bone cavity. The suture strand can be located on the same side of the anchor body to maximize the area of the anchor surface which engages bone, resulting in increased engagement into bone and resistance to tensile forces.

10 Claims, 11 Drawing Sheets

U.S. PATENT DOCUMENTS

| | | | |
|---|---|---|---|
| 5,597,579 | A | 1/1997 | Bezwada et al. |
| 5,607,687 | A | 3/1997 | Bezwada et al. |
| 5,618,314 | A * | 4/1997 | Harwin et al. ............ 606/232 |
| 5,618,552 | A | 4/1997 | Bezwada et al. |
| 5,620,698 | A | 4/1997 | Bezwada et al. |
| 5,645,850 | A | 7/1997 | Bezwada et al. |
| 5,648,088 | A | 7/1997 | Bezwada et al. |
| 5,683,418 | A | 11/1997 | Luscombe et al. |
| 5,698,213 | A | 12/1997 | Jamiolkowski et al. |
| 5,700,583 | A | 12/1997 | Jamiolkowski et al. |
| 5,733,307 | A | 3/1998 | Dinsdale |
| 5,782,863 | A * | 7/1998 | Bartlett ..................... 606/232 |
| 5,814,070 | A | 9/1998 | Borzone et al. |
| 5,859,150 | A | 1/1999 | Jamiolkowski et al. |
| 5,871,503 | A | 2/1999 | Bartlett |
| 5,891,168 | A * | 4/1999 | Thal ........................... 606/232 |
| 5,961,538 | A | 10/1999 | Pedlick et al. |
| 6,045,573 | A | 4/2000 | Wenstrom, Jr. et al. |
| 6,168,598 | B1 | 1/2001 | Martello |
| 6,270,518 | B1 | 8/2001 | Pedlick et al. |
| 6,306,158 | B1 | 10/2001 | Bartlett |
| 6,527,795 | B1 | 3/2003 | Lizardi |
| 6,610,080 | B2 | 8/2003 | Morgan |
| 6,773,436 | B2 | 8/2004 | Donnelly et al. |
| 7,875,064 | B2 | 1/2011 | Donnelly et al. |
| 2002/0004668 | A1 | 1/2002 | Bartlett |
| 2002/0007196 | A1 | 1/2002 | Bartlett |
| 2002/0120274 | A1 | 8/2002 | Overaker et al. |
| 2002/0161401 | A1 | 10/2002 | Steiner |

OTHER PUBLICATIONS

Heller, Handbook of Biodegradable Polymers, edited by Domb, et al, Hardwood Academic Press, pp. 99-118 (1997).

Journal of Biomaterials Research, vol. 22, pp. 993-1009, 1988 by Cohn and Younes.

Kemnitzer and Kohn, in the Handbook of Biodegradable Polymers, edited by Domb, et. al., Hardwood Academic Press, pp. 251-272 (1997).

Office Action dated May 14, 2003 in U.S. Appl. No. 09/967,473.

Office Action dated Nov. 4, 2003 in U.S. Appl. No. 09/967,473.

Polymer Preprints (ACS Division of Polymer Chemistry), vol. 30(1), p. 498, 1989 by Cohn.

U.S. Appl. No. 10/888,179—Advisory Action dated Feb. 5, 2008.

U.S. Appl. No. 10/888,179—Final Office Action dated Nov. 13, 2007.

U.S. Appl. No. 10/888,179—Final Office Action dated Sep. 4, 2008.

U.S. Appl. No. 10/888,179—Non-Final Office Action dated Jan. 13, 2010.

U.S. Appl. No. 10/888,179—Non-Final Office Action dated Jan. 23, 2009.

U.S. Appl. No. 10/888,179—Non-Final Office Action dated Mar. 11, 2008.

U.S. Appl. No. 10/888,179—Non-Final Office Action dated May 7, 2007.

U.S. Appl. No. 10/888,179—Non-Final Office Action dated Jul. 21, 2009.

U.S. Appl. No. 10/888,179—Notice of Allowance dated Jun. 15, 2010.

U.S. Appl. No. 10/888,179—Notice of Allowance dated Sep. 21, 2010.

Vandorpe, et al, Handbook of Biodegradable Polymers, edited by Domb, et al, Hardwood Academic Press, pp. 161-182 (1997).

* cited by examiner

ABSORBABLE BONE ANCHOR

CROSS-REFERENCE TO RELATED APPLICATIONS

This application is a continuation of U.S. patent application Ser. No. 10/888,179 filed on Jul. 9, 2004 and entitled "Absorbable Bone Anchor," now U.S. Pat. No. 7,875,064, which is a continuation of U.S. patent application Ser. No. 09/967,473 filed on Sep. 28, 2001 and entitled "Absorbable Bone Anchor," now U.S. Pat. No. 6,773,436. These references are hereby incorporated herein by reference in their entireties.

FIELD OF THE INVENTION

The invention relates generally to medical devices and procedures. More particularly, this invention relates to an absorbable bone anchor system for attaching soft tissue to hard bone, and to methods for attaching soft tissue to hard bone.

BACKGROUND OF THE INVENTION

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A number of devices and methods have been developed to attach soft tissue to bone. These include screws, staples, cement, suture anchors, and sutures alone. Some of the more successful methods involve use of a suture anchor to attach a suture to the bone, and tying the suture in a manner that holds the tissue in close proximity to the bone.

The tissue may be attached to the bone during open surgery, or during closed (e.g., arthroscopic) surgical procedures. Closed surgical procedures are preferred since they are less invasive and are less likely to cause patient trauma. In a closed surgical procedure, the surgeon performs diagnostic and therapeutic procedures at the surgical site through small incisions, called portals, using instruments specially designed for this purpose. One problem encountered in the less invasive, closed surgical procedures is that the surgeon has significantly less room to perform the required manipulations at the surgical site. Thus, devices and methods are needed which will allow a surgeon to effectively and easily attach tissue to bone in the small spaces provided by less invasive surgical procedures.

Proper attachment of soft tissue requires that it be placed in the anatomically correct position to promote optimal healing. Conventional methods for attaching soft tissue to bone have typically used toggling anchors having sutures attached thereto. The sutures enable the soft tissue to be adjustably tied down in proximity to the bone surface after the anchor is inserted in a predrilled bone cavity. However, the suture strands extending from the bone anchor can often encumber the area in which the bone anchor is introduced, leading to less than ideal engagement of the anchor in the cavity. In a situation where the bone cavity needs to be larger than the bone anchor to provide clearance for both the suture strands and the anchor, it is difficult to then effect sufficient engagement of the anchor to the bone.

There is thus a need for an improved system for anchoring soft tissue to bone which provides optimal purchase into bone to prevent loosening of the anchor in the bone cavity. Further, there is a need for an improved system for anchoring soft tissue to hard bone which enables suture strands to be located on the same side of the anchor body in order to maximize the area of the leading surface of the bone anchor which engages bone, resulting in increased engagement and resistance to tensile forces. It would also be advantageous to provide a fully absorbable suture anchor and system.

SUMMARY OF THE INVENTION

The present invention avoids the aforementioned problems associated with conventional toggling anchors by providing a bone anchor that can toggle in two planes for secure anchorage within a bone cavity. The bone anchor is configured such that the suture strands can be located on the same side of the anchor body to maximize the area of the leading surface which engages bone, resulting in increased engagement and resistance to tensile forces.

In an exemplary embodiment of the present invention, a bone anchor is provided for anchoring tissue to bone having an elongate body extending between a first leading end and a second trailing end. The elongate body defines a longitudinal axis of the anchor. Between the first and second ends are two opposed surfaces and a plurality of sidewalls adjacent to and extending between the two opposed surfaces. Extending from one of the sidewalls is a flared portion configured to engage and anchor into bone. The elongate body also includes at least one suture channel for passage of a suture strand therethrough. The suture channel is obliquely angled with respect to the longitudinal axis such that applying tension to a suture strand extending through the suture channel will force the bone anchor to toggle in two planes. This two-way toggling action enables a better interference fit of the bone anchor in the bone cavity.

In one aspect of the present invention, the bone anchor may include a notch for engaging a portion of the suture strand. The anchor may also include two suture channels. Preferably, the suture channels are misaligned with respect to the longitudinal axis of the body. A fin extending from one of the sidewalls can also be included.

In another aspect of the present invention, the bone anchor can include an elevated region that includes extra material near the first leading end of the body. Bone anchor can also include a depressed region near the second trailing end wherein material is removed from this depressed region to provide clearance for the suture thread.

In a preferred embodiment, the bone anchor can be entirely bioabsorbable. However, the bone anchor may also be formed of a non-absorbable polymer or metal. A method is also provided by which a detached tissue may be securely attached to bone in an anatomically correct position using the bone anchor of the present invention.

Further features of the invention, its nature and various advantages, will be more apparent from the accompanying drawings and the following detailed description of the drawings and the preferred embodiments.

DETAILED DESCRIPTION OF THE DRAWINGS

Figure 1A:
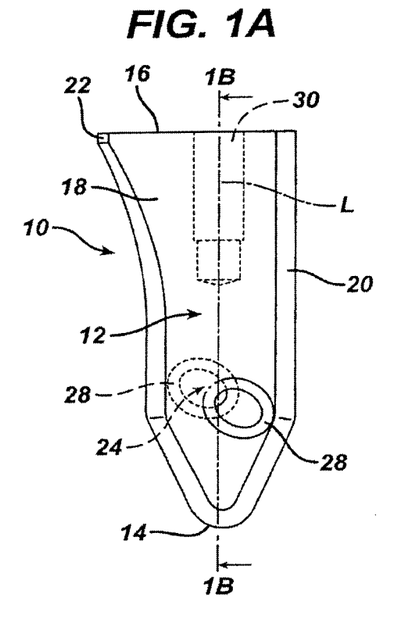
FIG. 1A is a cross-sectional view of an embodiment of the bone anchor of the present invention.
Figure 1B:
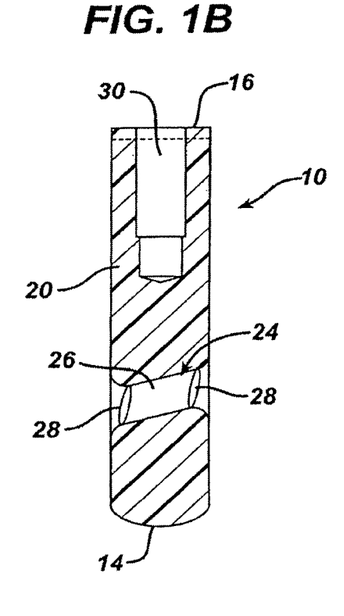
FIG. 1B is another cross-sectional view through the side of the bone anchor of FIG. 1A at lines 1B-1B.
Figure 1C:
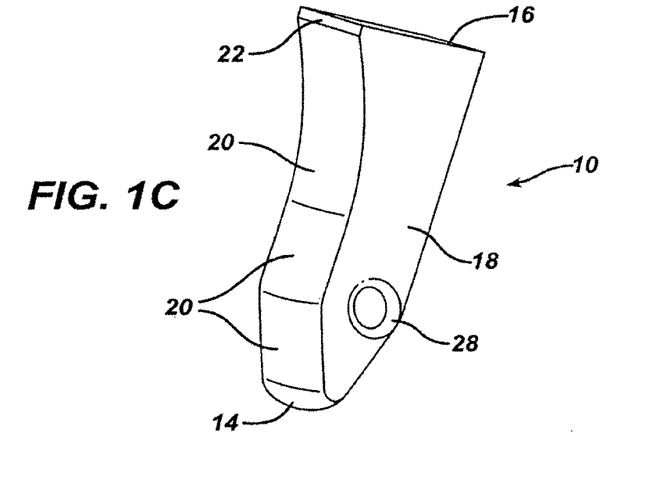
FIG. 1C is a perspective view of the bone anchor of FIG. 1A.

Referring to FIG. 1A, an exemplary bone anchor 10 of the present invention is shown having an elongate body 12 extending between a first leading end 14 and a second trailing end 16 for defining a longitudinal axis L. First leading end 14 may be tapered as shown. The elongate body 12 comprises two opposed surfaces 18 that extend between the ends 14, 16, and a plurality of sidewalls 20 adjacent to and extending between the two opposed surfaces 18, as shown in FIG. 1C. Near the second trailing end 16 and extending from one of the plurality of sidewalls 20 is a flared portion 22. The flared portion 22 lends an asymmetric profile to the bone anchor 10 and facilitates the toggling action of the bone anchor 10 once inserted inside a bone cavity. Flared portion 22 may have a sharp edge for penetrating into bone, though the edge does not have to be a knife edge to effectively engage the walls of the bone cavity.

Although surfaces 18 are shown as flat, it is understood that they may be otherwise shaped or contoured. For example, they may be curved or rounded. Surfaces 18 may also include surface features such as roughened portions, or protrusions, that facilitate anchorage of the bone anchor 10 into the bone cavity. The sidewalls 20 that are adjacent to surfaces 18 may also be curved, rounded, or flat.

Elongate body 12 also includes a suture channel 24 for passage of a suture strand through the bone anchor 10. As shown in FIG. 1B, suture channel 24 comprises a through-hole 26 extending through each of the opposed surfaces 18 of bone anchor 10. Through-hole 26 extends into a recessed opening 28 at each of the surfaces 18, as best illustrated in FIG. 1C. Each of the recessed openings 28 is elliptically shaped, or ovoid, as shown in FIG. 1A. Recessed opening 28 helps enable as much of the suture strand to lie flush with respect to surface 18 of the bone anchor 10 as possible, alleviating suture binding and pinching of the suture strand between the anchor 10 and bone cavity. Recessed openings 28 also reduce friction against the suture strand when tension is applied. Suture channel 24 is obliquely angled with respect to the longitudinal axis L of the body 12, as shown in FIGS. 1A and 1B. Thus, the recessed openings 28 of the suture channel 24 on opposed surfaces 18 do not line up.

Because of the uniquely angled suture channel 24 of bone anchor 10, a suture strand extending through this channel 24 can effect a toggling action in the bone anchor 10 in two planes when tension is applied. This toggling action is enhanced by having the suture strand pass through the surfaces 18 of the anchor 10, rather than through the sides 20. In addition, the two-way toggling action resulting from the configuration of the suture channel 24 enables purchase of the entire length of the flared portion 22 into bone, rather than just a corner of the anchor 10, or a small portion of the flared portion 22 as with conventional bone anchors with bone engagement edges. The increased surface area that can be anchored into bone results in increased resistance of the anchor 10 to being pulled out with a tensile force. The increased surface area also enables the bone anchor 10 to achieve purchase in a wider range of bone hardness, since the engagement force into bone can now be distributed over a wider surface area, without the potential of shearing off the flared portion 22 or cutting through the bone such as occurs with conventional bone anchors having small bone engagement edges. Ultimately, these features result in a bone anchor 10 having an overall size which is smaller than conventional bone anchors while still being able to achieve optimal bone purchase. For instance, the anchor 10 of the present invention can have a diameter in the range of about 3.0 mm.

In addition to pulling on a suture strand 2 extending from the obliquely angled suture channel 24, bone anchor 10 can be toggled using an inserter tool (not shown). As illustrated in FIG. 1A, extending from the second trailing end 16 into elongate body 12 is a bore 30 configured to engage with a distal end of an inserter tool. Bore 30 can be threaded to threadably engage the inserter tool. When tension and deflection by the inserter is applied to the bone anchor 10, after the anchor is positioned within bone, the anchor 10 undergoes a toggling action, or rotation which results in the anchor 10 being oriented in a direction that is not parallel with the longitudinal axis of the anchor-seating bore 30. This toggling of the anchor 10 causes the anchor 10 to become lodged within the bone. Thus, toggling of the bone anchor 10 can be achieved by tensioning the suture strand in the suture channel 24 and/or mechanically deflecting the bone anchor 10 with the inserter tool. Both techniques can work in synchrony to create an optimal interference fit of the anchor 10 within a bone cavity.

Bone anchor 10 of the present invention can be formed of a bioabsorbable material. This provides the benefit of reducing immunological problems associated with having a foreign substance within the body over a prolonged period of time. Bone anchor 10 can be composed of a suitable copolymer combination such as polylactic acid-polyglycolic acid (PLA-PGA), with a predominant fraction of PGA. Other bioabsorbable polymers can be used to make the annular member according to the present invention. Examples of suitable biocompatible, bioabsorbable polymers include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, (-valerolactone, &-butyrolactone, (-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, ∀,∀-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly (iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and, -caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Exemplary bioabsorbable, biocompatible elastomers include but are not limited to elastomeric copolymers of ε-caprolactone and glycolide (including polyglycolic acid) with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of, -caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable bioabsorbable elastomers are described in U.S. Pat. Nos. 4,045,418; 4,057,537 and 5,468,253.

Preferably, the anchor 10 is formed from polylactic acid, or a composite blend of tricalcium phosphate and polylactic acid. However, it is contemplated that bone anchor 10 of the present invention can also be made of non-absorbable materials. For example, the bone anchor 10 may be made of polysulfone, or a metal such as Titanium 6A1-4V.

Figure 2A:
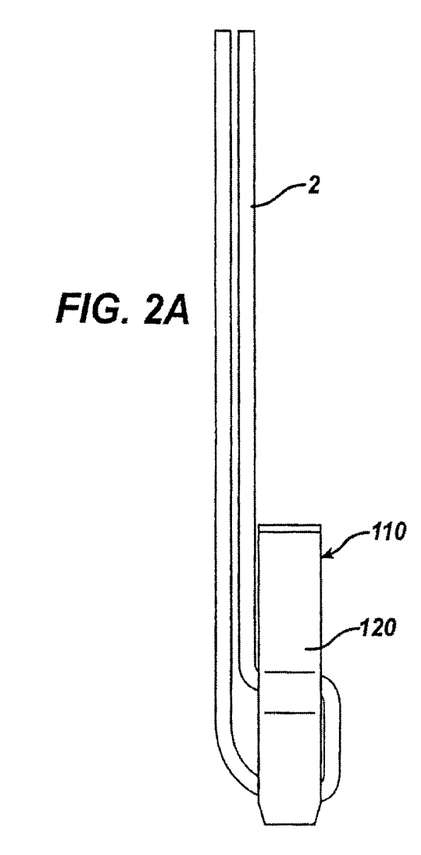
FIG. 2A is a side view of another embodiment of the bone anchor of the present invention.
Figure 2B:
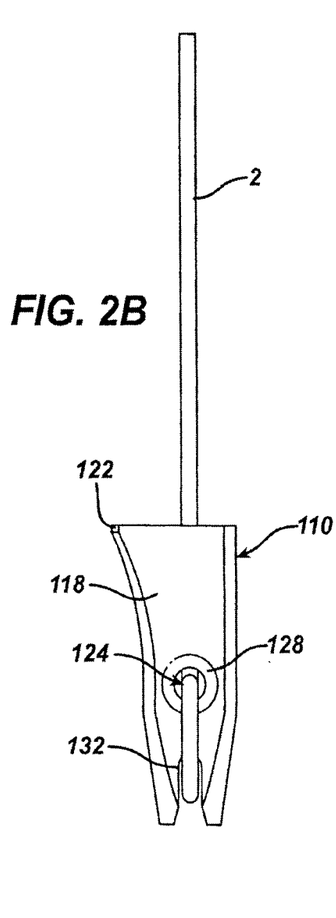
FIG. 2B is a surface view of the bone anchor of FIG. 2A.
Figure 2C:
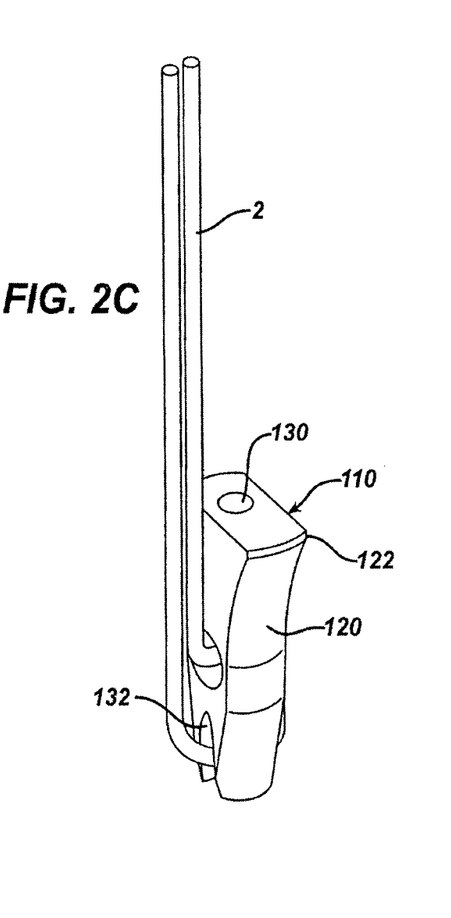
FIG. 2D is a cross-sectional view of another embodiment of the bone anchor of the present invention.
Figure 2D:
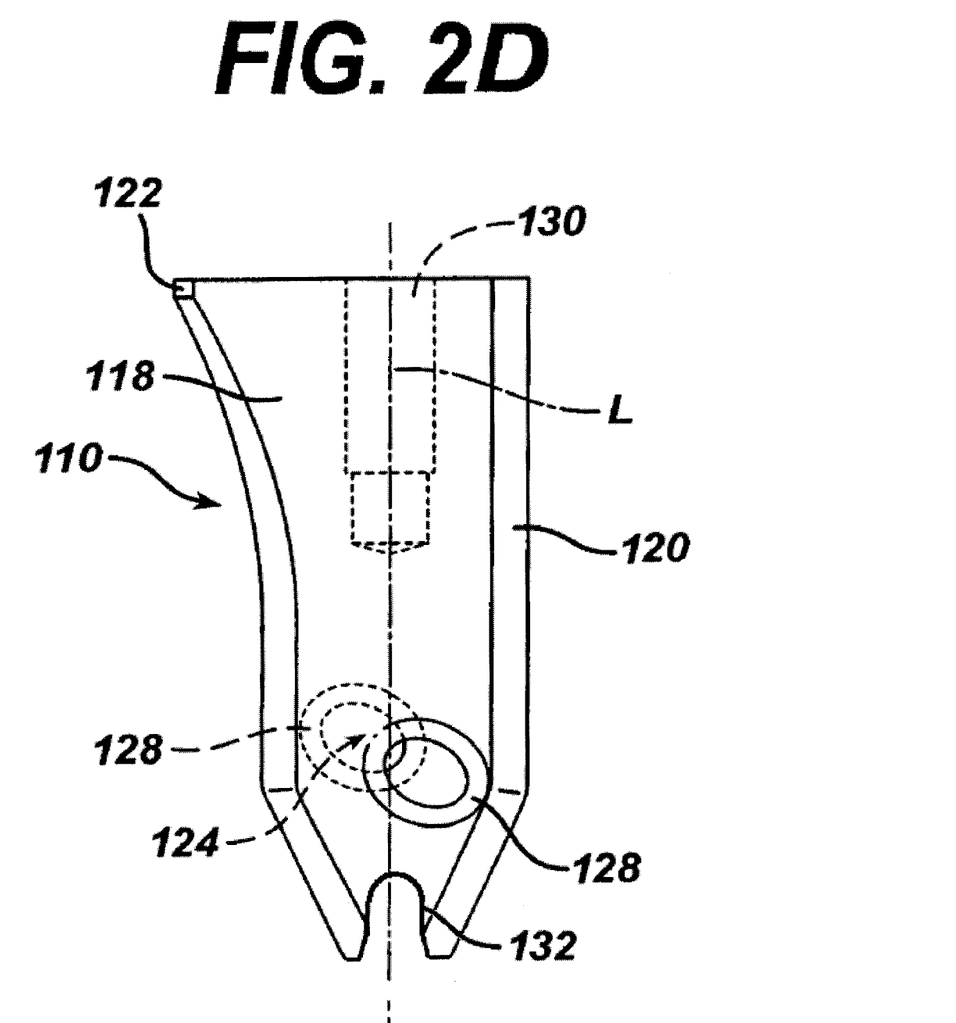

Rather than having a closed nose at first leading end 14, the bone anchor 10 can have an open nose. As shown in FIGS. 2B through 2D, bone anchor 110 has the same features of anchor 10, with similar elements being designated by the same number with the prefix "1". Most notably, bone anchor 110 has a suture engaging notch 132 at its distal end 114. Suture engaging notch 132 allows the suture strand 2 passing through suture channel 124 to enter and exit on the same side of the bone anchor, as illustrated in FIGS. 2A and 2C.

Figure 3A:
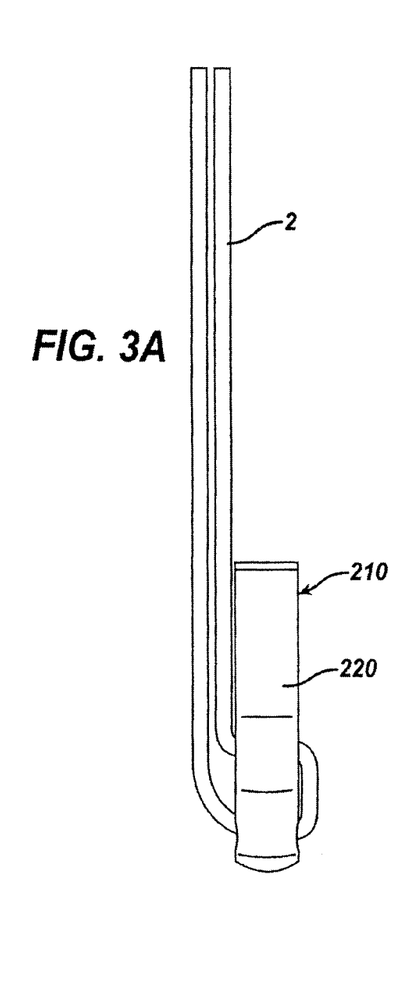
FIG. 3A is a side view of yet another embodiment of the bone anchor of the present invention.
Figure 3B:
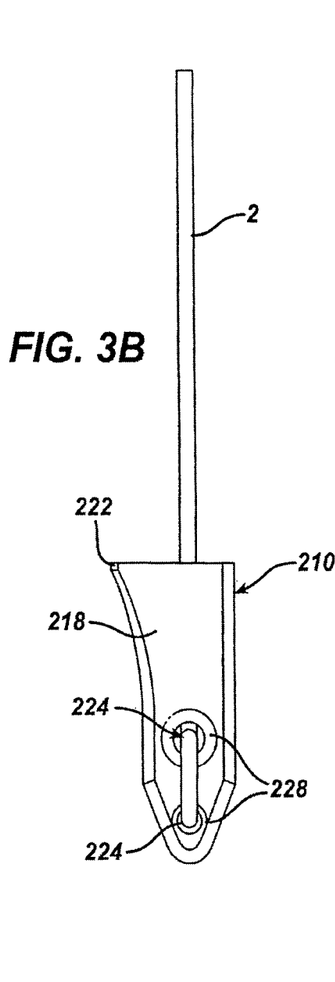
FIG. 3B is a surface view of the bone anchor of FIG. 3A.
Figure 3C:
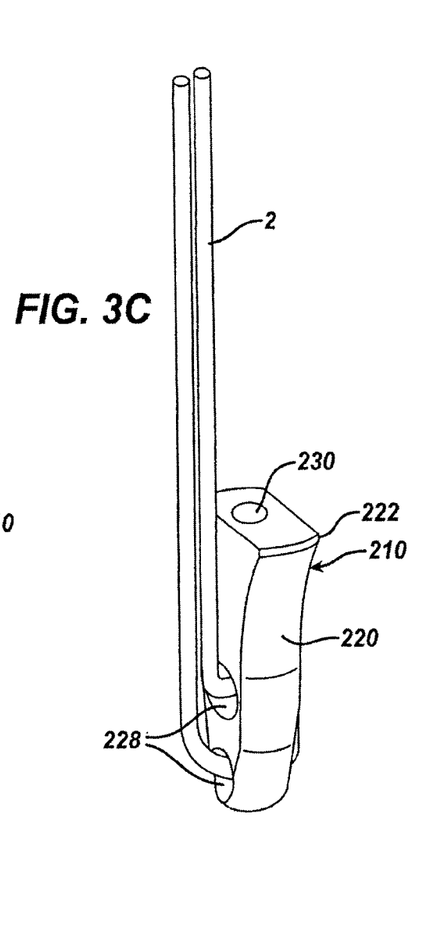
FIG. 3C is a perspective view of the bone anchor of FIG. 3A.

FIGS. 3A-3C show yet another embodiment of the present invention in which bone anchor 210 has two suture channels 224. The two suture channels 224 enable the suture strand 2 to enter and exit the bone anchor 10 on the same side, as illustrated in FIGS. 3A and 3C. In all other respects, bone anchor 210 has the same features of anchor 10, with similar elements being designated by the same number with the prefix "2".

Figure 4A:
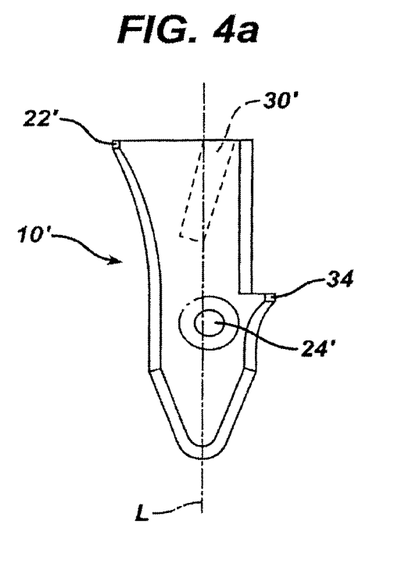
FIG. 4A is a cross-sectional view of another embodiment of the bone anchor of the present invention.

In another aspect of the present invention, bone anchor 10' includes all the features of bone anchor 10, with similar elements being designated with the same numbers followed by the suffix "'", but can also include a fin 34, as shown in FIG. 4A. Fin 34 extends from a sidewall 20' at approximately midway between the distal end 14' and proximal end 16' of the bone anchor 10'. Fin 34 acts as a shovel, providing an additional ledge for digging into bone and preventing the anchor 10' from accidentally pulling out. In extra hard bone, the fin 34 can serve as a compression fit element. Though fin 34 may not need to be a knife edge, fin 34 should have a sharp edge for penetrating into bony tissue.

Bone anchor 10' also includes a bore 30' that extends at an angle with respect to the longitudinal axis L for engagement with an inserter tool. The bore 30' can have an angle in the range of about 15° from the longitudinal axis L of the bone anchor 10'. Such an angled bore 30' may provide additional leverage for toggling the bone anchor 10' inside the bone cavity when the inserter tool is attached.

Figure 4B:
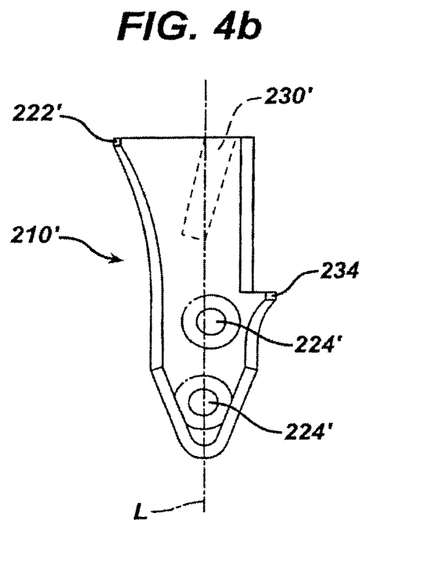
FIG. 4B is a cross-sectional view of another embodiment of the bone anchor of the present invention.

The additional features present in bone anchor 10' may also be included in bone anchor 210', shown in FIG. 4B. Bone anchor 210' can also have a fin 234 and a longitudinally offset, or angled bore 230'. Further, in bone anchor 210' each of the suture channels 224' is misaligned with respect to the longitudinal axis L. That is, the recessed openings 228' of the suture channels 224' do not line up along the longitudinal axis, but are rather staggered with respect to the longitudinal axis L. It is understood that bone anchor 210' shares similar features with bone anchor 210, the same features being designated with the same number followed by the suffix "'".

Figure 5:
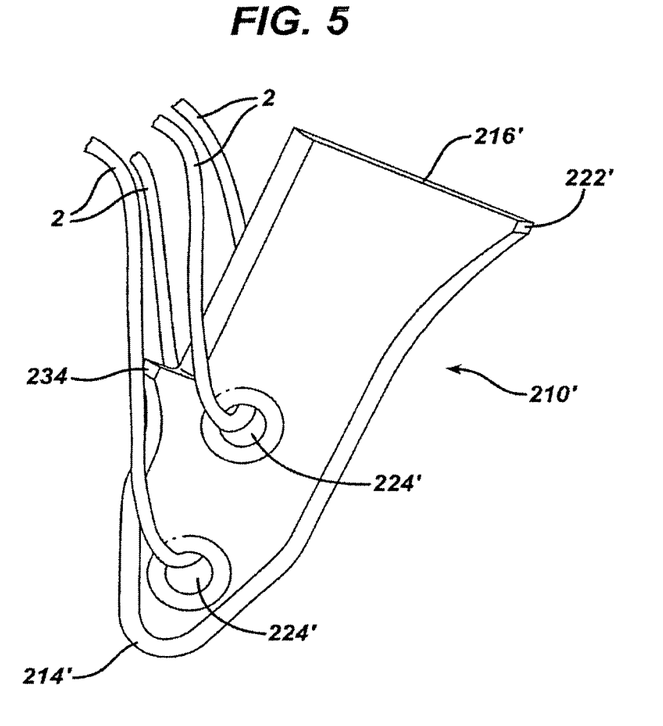
FIG. 5 depicts the bone anchor of FIG. 4B with two suture strands.

It is contemplated that bone anchors 210, 210' can be used with two suture strands 2. As depicted in FIG. 5, bone anchor 210' can be threaded with a suture strand 2 in each suture channel 224. By providing the bone anchor 210' with two suture strands, more precise and controlled toggling can be achieved as individual strands 2 are manipulated at separate times and with differing amounts of tension. Since the suture channels 224' are not aligned longitudinally, this enables two suture strands 2 to be threaded through without substantial overlap or encumbrance of suture strands 2 on the surface 218' of the bone anchor 210' where all the free ends of the strands 2 exit.

FIGS. 6A-6C, 7A, and 7B illustrate yet another embodiment of the bone anchor 310 of the present invention. Building on the features of bone anchor 210', bone anchor 310 includes fin 334 and two suture channels 324. In addition, bone anchor 310 includes an elevated region 338 surrounding leading end 314. Elevated region 338 includes both the surfaces 318 and sides 320. The increased material in this elevated region 338 prevents over-rotation or flipping of the bone anchor 310 in the bone cavity. Furthermore, the additional material helps clean bone debris as the anchor 310 is inserted into the cavity.

Figure 6A:
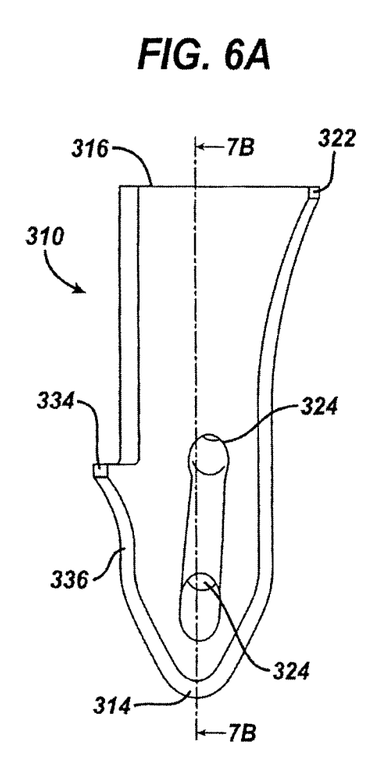
FIG. 6A is a surface view of yet another embodiment of the bone anchor of the present invention.
Figure 6B:
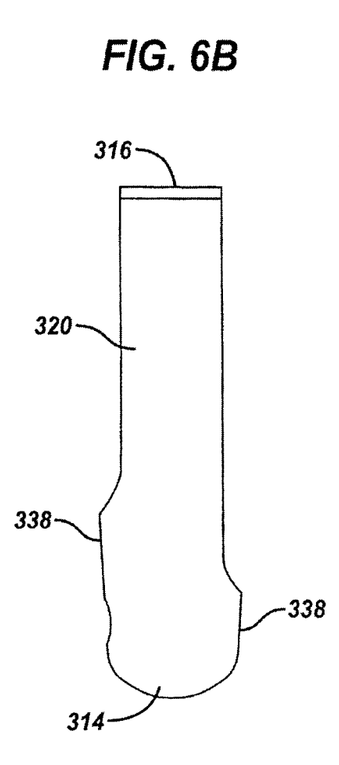
FIG. 6B is a side view of the bone anchor of FIG. 6A.
Figure 6C:
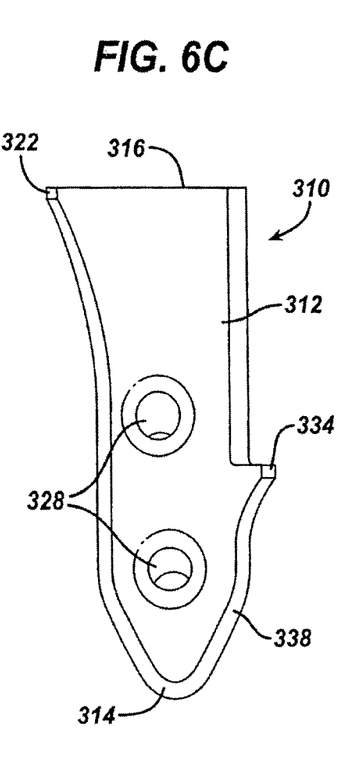
FIG. 6C is another surface view of the bone anchor of FIG. 6A.
Figure 7A:
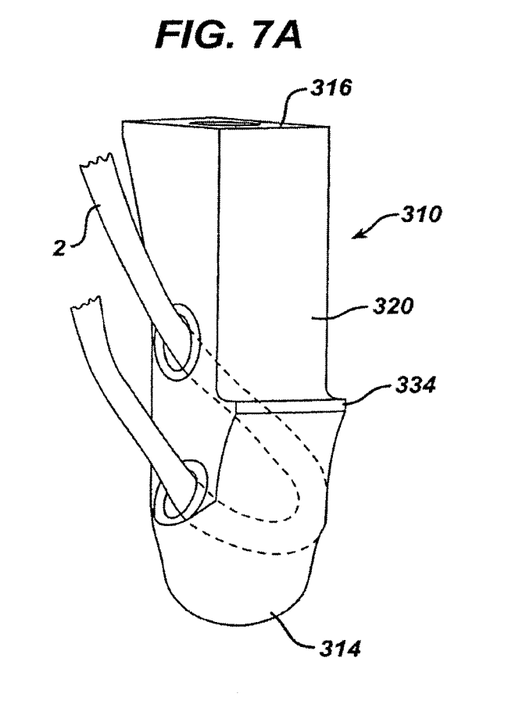
FIG. 7A is a perspective view of the bone anchor of FIG. 6A with a suture strand.
Figure 7B:
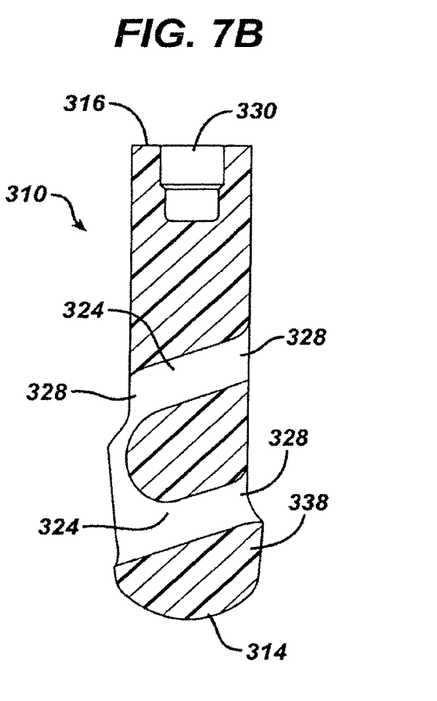
FIG. 7B is a cross-sectional view of the bone anchor of FIG. 6A at lines 7B-7B-.

As shown in FIG. 6A, the additional material forming elevated region 338 surrounding the two suture channels 324 creates a trough 334 within the elevated region 338. Trough 336 connects an opening 328 of one of the suture channels 324 with the other opening 328 of the second suture channel 324. The trough 336 enables a portion of a suture strand 2 that passes from one opening 328 to another opening 328 to seat against the body 312 of the bone anchor 310. FIG. 7A shows a perspective view of bone anchor 310 having a suture strand 2 passing through the channels 324. As illustrated in FIG. 7B, the combination of the two suture channels 324 and trough 336 provide a smooth passageway for a suture strand to pass therethrough, without excess friction. The smoothness of the passageway and angled channel openings 328 enhances the slidability of the suture strand therethrough. In addition, the large radius of curvature of the suture passageway formed by the two suture channels 324 and trough 336 facilitates ease of suture movement.

Figure 8A:
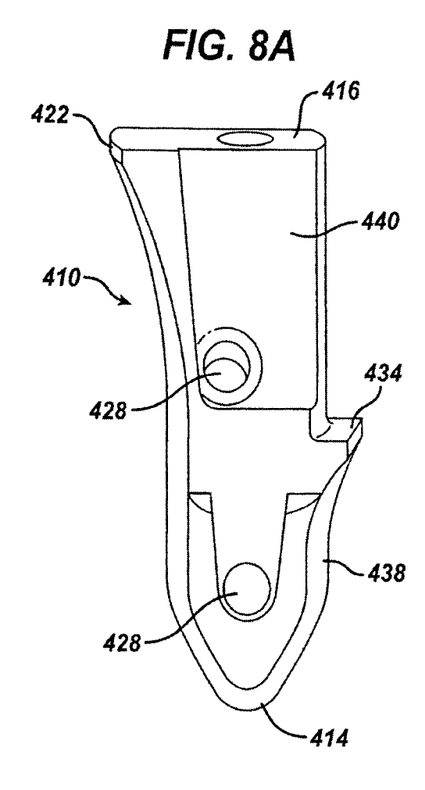
FIG. 8A is a surface view of yet another embodiment of the bone anchor of the present invention.
Figure 8B:
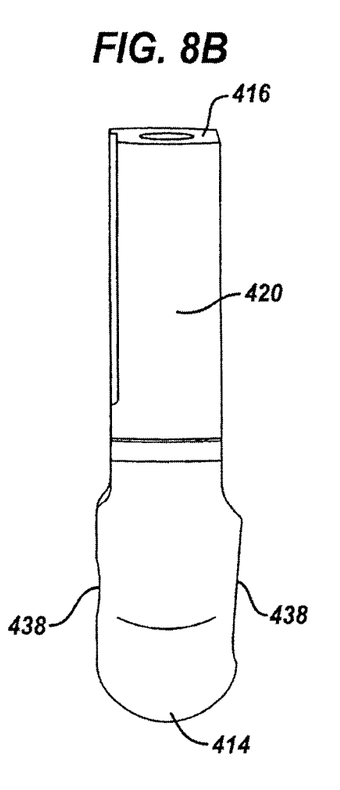
FIG. 8B is a side view of the bone anchor of FIG. 8A.
Figure 8C:
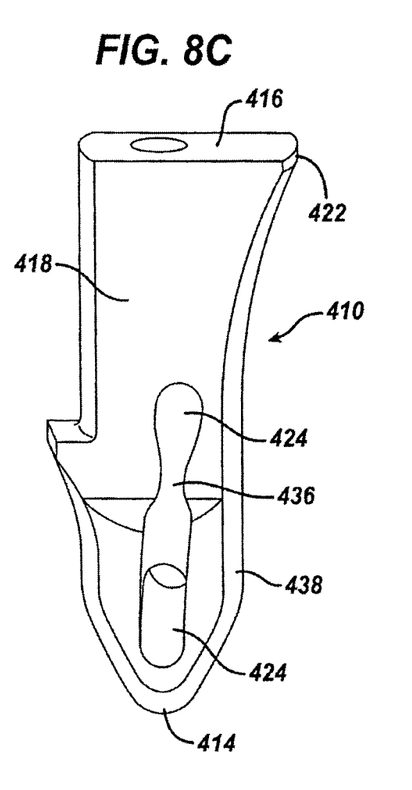
FIG. 8C is another surface view of the bone anchor of FIG. 8A.

In yet another embodiment of the present invention, the bone anchor 410 can include not only an elevated region 436 but a depressed region 438. As shown in FIGS. 8A and 8B, bone anchor 410 includes near the second trailing end 416 a depressed region 440 wherein material is removed from one of the surfaces 418. An opening 428 of one of the two suture channels 424 is located within this depressed region 440. The depressed region 440 provides clearance for the suture strand to lie against the body 412 of the bone anchor 410. Together with the trough 434 on the opposite surface 418, shown in FIG. 8C, the depressed region 438 helps maintain the slim profile of the bone anchor system of the present invention.

The anchors 10, 10' 110, 210, 210', 310, and 410 of the present invention may be used in the method described herein below for anchoring tissue to bone. For purposes of illustration, FIGS. 9A-9D depict the method of using suture 410 in the context of an arthroscopic shoulder repair, more specifically, attaching a detached labrum (as might result from a Bankart lesion or rotator cuff tear) to the glenoid rim of a scapula. It will be understood, however, that the system and method described herein are equally applicable to connecting detached tissue in other contexts as well. Further, the method described is merely exemplary of the steps involved in using any of the embodiments of the anchors of the present invention, and is equally suitable for anchors 10, 10', 110, 210, 210', and 310.

Figure 9A:
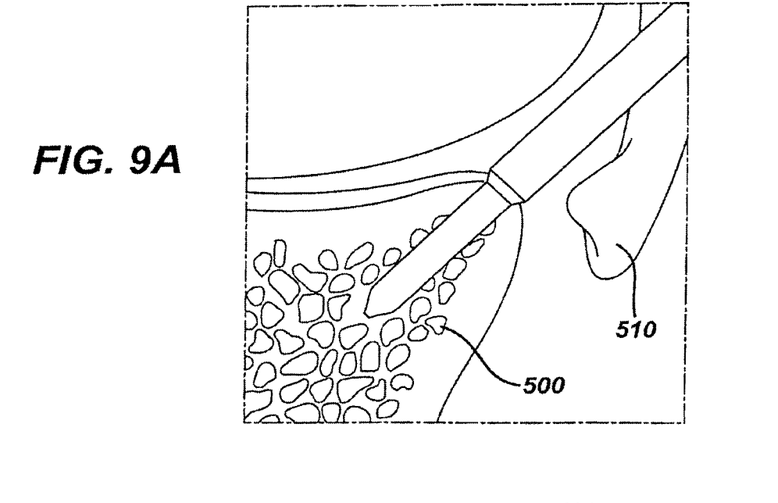
FIG. 9A depicts a step in the method of deploying the bone anchor of the present invention.
Figure 9B:
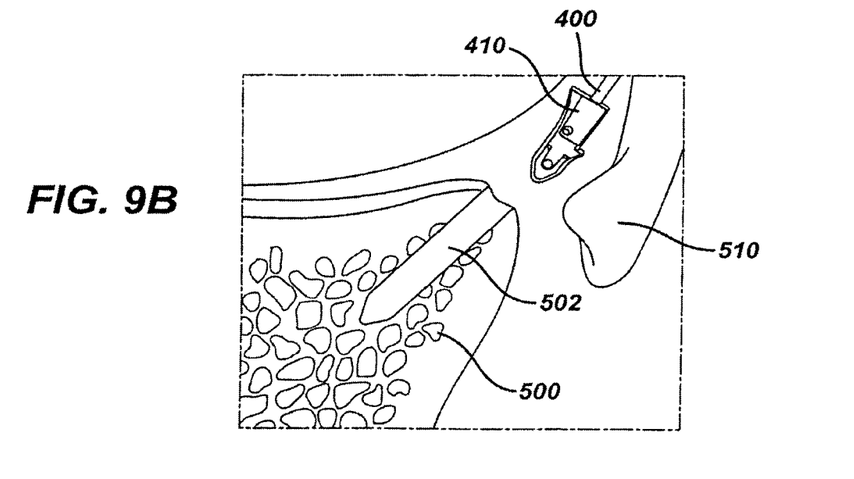
FIG. 9B depicts another step in the method of deploying the bone anchor of the present invention.
Figure 9C:
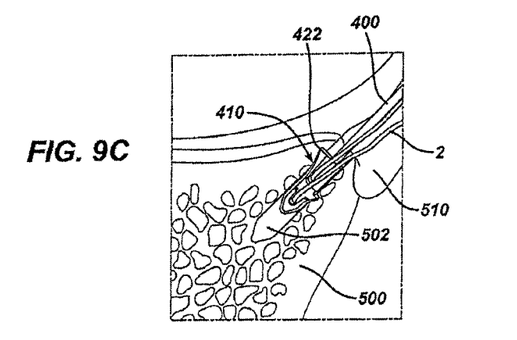
FIG. 9C depicts yet another step in the method of deploying the bone anchor of the present invention.
Figure 9D:
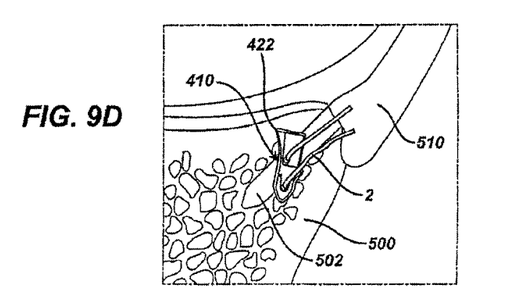
FIG. 9D depicts a final step in the method of deploying the bone anchor of the present invention.
Figure 9E:
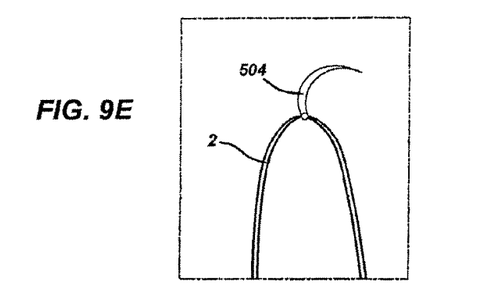
FIG. 9E depicts the suture of FIGS. 9A-9D with a needle attached thereto.

Referring to FIG. 9A, a bore 502 is formed in bone 500 of the patient. The diameter of the bore 502 should be about the same size as the largest outer diameter of the bone anchor 410, e.g., about 3.0 mm. The length of the bore 502 should be of sufficient length to allow for complete seating of the suture anchor 410. As shown in FIG. 9B, an inserter tool 400 can be attached to bone anchor 410 for tapping the anchor 410 into the bore 502. Bone anchor 410 can be provided with an open suture, i.e., a suture strand extending therethrough, or, as shown in FIG. 9E, with a suture having a needle 504 already attached for bringing soft tissue 510 in proximity to the bony structure 500 for reattachment. The suture needle 504 can have a first, tissue penetrating end and a second, trailing end attached to a loop of suture thread 2 extending through bone anchor 410.

In. FIG. 9C, the suture thread 2 extending from bone anchor 410 has been threaded through the free end of detached labrum 510 using any conventional method known in the surgical art. The bone anchor 410 can then be tapped into bore 502, bringing the detached labrum 510 in proximity to shoulder bone 500. Because the top portion of the anchor 410 is sized very close to the diameter of the bone cavity 502, there results an interference fit in this area when the anchor 410 is placed within the bore 502. This tight fit also allows the anchor 410 to pivot in place when a tensile force is placed on the suture strands. It is contemplated that applying force on the inserter tool 400 can effect toggling of the bone anchor 410 while inside the bore 502. In certain situations, it may be desirable to perform this step to provide additional securement of the bone anchor 410 prior to effecting additional toggling by pulling on the suture thread 2.

Once the bone anchor 410 is properly inserted and the detached labrum 510 is in position, the inserter tool 400 can be removed. The free ends of suture thread 2 can be pulled to apply tension to the suture 2 seated within the bone anchor 410. The anchor will toggle, e.g., about 90° with respect to the location of the suture strands 2. This toggling action can result in the flared portion 422 of the anchor 410 being lodged into the side of the bone cavity 502. The body 412 of the anchor 410 is designed in such a way as to maximize the surface area of this second trailing end 416. The bone anchor 410 is thus stabilized in an interference fit within the bore 502, and the detached labrum 510 is thereby attached to the shoulder bone 500 in the desired position, as illustrated in FIG. 9D. Free ends of suture thread 2 can then be secured together and the excess trimmed as is typical in these situations to complete the surgery.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A system for anchoring tissue to bone, comprising:
   a bone anchor comprising an elongate body having
      an open tapered leading end with a suture engaging notch formed therein, a trailing end with a flared sidewall configured to engage bone, and a suture channel extending through opposed sidewalls of the elongate body at a location between the leading and trailing ends; and a loop of suture thread extending through the suture channel;

wherein the suture channel is obliquely angled with respect to a central longitudinal axis of the bone anchor such that, when the bone anchor is disposed within a bone hole and tension is applied to the loop of suture thread, the bone anchor will toggle in two planes; and wherein the suture channel defines opposed first and second openings, the first opening is positioned closer to the leading end than the second opening, and the first and second openings are laterally offset from one another relative to a longitudinal axis extending between the leading and trailing ends of the elongate body.

2. The system of claim 1, further comprising a suture needle having a first, tissue penetrating end and a second, trailing end that is attached to the loop of suture thread.

3. The system of claim 1, wherein the first and second openings are recessed related to an outer surface of the elongate body.

4. A bone anchor for anchoring tissue to bone, comprising:

an elongate body having a central longitudinal axis extending between a leading end and a trailing end, first and second opposed substantially planar surfaces that extend between the leading and trailing ends, and third and fourth sidewalls that extend between the leading and trailing ends and the first and second opposed substantially planar surfaces, wherein a width between the third and fourth sidewalls increases from the leading end to the trailing end;

at least one suture channel extending through the first and second opposed substantially planar surfaces of the elongate body for passage of a suture strand therethrough, the at least one suture channel being obliquely angled with respect to the central longitudinal axis of the elongate body such that applying tension to a suture passed therethrough when the bone anchor is disposed in a bone hole is effective to toggle the bone anchor in two planes; and an open suture engaging notch formed in the leading end;

wherein the suture channel extends between first and second openings formed in the first and second opposed substantially planar surfaces of the elongate body and wherein the first and second openings are both longitudinally and laterally offset from one another.

5. The bone anchor of claim 4, wherein the first and second openings are recessed with respect to the first and second opposed substantially planar surfaces of the elongate body.

6. The bone anchor of claim 4, wherein the open suture engaging notch extends through the first and second opposed substantially planar surfaces of the elongate body.

7. The bone anchor of claim 4, wherein one of the third and fourth sidewalls extends laterally outward to define a flared portion configured to engage bone.

8. A method for anchoring tissue to bone, comprising:

forming a bone cavity within a bony structure;

threading a needle through a free end of tissue such that a first end of a suture loop attached to the needle is positioned on a first side of the tissue, and a second end of the suture loop attached to a bone anchor is positioned on a second side of the tissue;

inserting the bone anchor with the suture loop attached thereto into the bone cavity, the suture loop extending through a suture channel formed in the bone anchor;

applying tension to the suture loop to toggle the bone anchor in two planes within the bone cavity, thereby causing a flared portion of the bone anchor to extend into and engage the bone cavity; and tying the suture loop to bring the free end of the tissue proximate to the bony structure.

9. The method of claim 8, wherein the suture channel includes opposed openings formed in opposed sidewalls of the bone anchor, the opposed openings being both laterally and longitudinally offset from one another to allow the suture anchor to toggle in two planes when tension is applied to the suture loop.

10. The method of claim 8, further comprising, prior to inserting the bone anchor, coupling the bone anchor to an inserter tool.

* * * * *